United States Patent [19]

Armistead et al.

[11] Patent Number: 5,516,797
[45] Date of Patent: May 14, 1996

[54] IMMUNOSUPPRESSIVE COMPOUNDS

[75] Inventors: David M. Armistead, Maynard; Joshua S. Boger, Concord; Harold V. Meyers, Belmont; Jeffrey O. Saunders, Acton; Roger D. Tung, Cambridge, all of Mass.

[73] Assignee: Vertex Pharmaceuticals, Incorporated, Cambridge, Mass.

[21] Appl. No.: 226,011

[22] Filed: Apr. 11, 1994

Related U.S. Application Data

[63] Continuation of Ser. No. 724,734, Jul. 2, 1991, Pat. No. 5,330,993, which is a continuation-in-part of Ser. No. 547,814, Jul. 2, 1990, Pat. No. 5,192,773.

[51] Int. Cl.$^6$ .................... A61K 31/445; A61K 31/40; A61K 31/22; A61K 31/24

[52] U.S. Cl. .................... 514/548; 514/330; 514/423; 514/428; 514/534; 514/538; 514/547; 514/549; 514/551; 514/465; 514/466; 549/441; 560/39; 560/43; 560/170

[58] Field of Search .................... 514/538, 534, 514/547, 548, 549, 551, 465, 466, 885; 549/441; 560/39, 43, 170

[56] References Cited

FOREIGN PATENT DOCUMENTS 0196841 10/1986 European Pat. Off. .
2328391 1/1974 Germany .

OTHER PUBLICATIONS

G. Blaschke et. al., "Investigation of Chromatographic Resolutions of Racemates, VI. Polymeric Amino Acid Derivatives As Optically Active Adsorbents", *Chem. Ber.*, 109(6), pp. 1967–1975 (1976).
A. Boulmedais et. al., "Stereochemistry of Electrochemical Reduction of Optically Active Alfa–Ketoamides. II. Electro–Reduction of Benzoylformamides Derived from S–(–)–Proline", *Bull. Soc. Chim. Fr.*, 2, pp. 189–191 (1989).
R. S. Coleman et. al., "Degradation and Manipulations of the Immunosuppressant FK506: Preparation of Potential Synthetic Intermediates", *Heterocycles*, 28, pp. 157–161 (1989).
F. Effenberger et. al., "Amino Acids. 14. Diastereoselective Addition of Benzenesulfenyl Chloride to 1–Acryloylproline Esters", *Chem. Ber.*, 122(3), pp. 545–551 (1989).
M. Egbertson and S. J. Danishefsky, "Synthetic Route to the Tricarbonyl Region of FK–506", *J. Org. Chem.* 54, pp. 11–12 (1989).

G. Feutren, "The Optimal Use of Cyclosporin A in Autoimmune Diseases", *J. Autoimmun.*, 5, pp. 183–195 (1992).
R. W. Finberg et. al., "Prevention of HIV–1 Infection and Preservation of CD4 Function by the Binding of CPFs to gp120", *Science*, 249, pp. 287–291 (1990).
L. Fry, "Psoriasis: Immunopathology and Long–term Treatment with Cyclosporin", *J. Autoimmun.*, 5, pp. 277–283 (1982).
M. W. Harding et. al., "A Receptor for the Immunosuppressant FK–506 is a Cis–Trans Peptidyl–Prolyl Isomerase", *Nature*, 341, pp. 758–760 (1989).
B. U. Kaczmar et. al., "Snake–Cage Polymers, 1. Synthesis of Various Snake–Cage Polyelectrolytes Consisting of Polyacrylamides and an Anion Exchanger", *Makromol. Chem.*, 177(7), pp. 1981–1989 (1976).
C. Ponticelli, "Treatment of the Nephrotic Syndrome with Cyclosporin A", *J. Autoimmun.*, 5, pp. 315–324 (1992).
K. Soai et. al., "Diastereoselective Asymmetric Allylation of Chiral α–Keto–amides with Allyltrimethylsilane. Preparation of Protected Homoallylic Alcohols", *J. Chem. Commun.*, 4, pp. 769–772 (1984).
K. Soai et. al., "Diastereoselective Reduction of Chiral Alpha–Ketoamides Derived from (S)–Proline Esters with Sodium Borohydride. Preparation of Optically Active Alpha–Hydroxy Acids", *J. Chem. Soc., Perkins Trans.*, 4, pp. 769–772 (1985).
R. S. A Tindall, "Immunointervention with Cyclosporin A in Autoimmune Neurological Disorders", *J. Autoimmun.*, 5, pp. 301–313 (1992).
P. Tugwell, "Cyclosporin in the Treatment of Rheumatoid Arthritis", *J. Autoimmun.*, 5, pp. 231–240 (1992).
D. R. Williams et. al., "Synthesis of the α,β–Diketo Amide Segment of the Novel Immuno Suppressive FK506", *J. Org. Chem.*, 53, pp. (1988).

*Primary Examiner*—Peter O'Sullivan
*Attorney, Agent, or Firm*—James F. Haley, Jr.; Leslie A. McDonell; Andrew S. Marks

[57] ABSTRACT

This invention relates to a novel class of immunosuppressive compounds having an affinity for the FK-506 binding protein (FKBP). Once bound to this protein, the immunosuppressive compounds inhibit the prolyl peptidyl cis-trans isomerase (rotamase) activity of the FKBP and inhibit T cell activation. As such, the compounds of this invention can be used as immunosuppressive drugs to prevent or significantly reduce graft rejection in bone marrow and organ transplantations and for use in the treatment of a wide variety of autoimmune diseases in humans and other mammals.

8 Claims, 2 Drawing Sheets

IMMUNOSUPPRESSIVE COMPOUNDS

CROSS REFERENCE TO PRIOR APPLICATIONS

This is a continuation of application Ser. No. 07/724,734, filed Jul. 2, 1991, now U.S. Pat. No. 5,330,993, which is a continuation-in-part of application Ser. No. 07/547,814, filed Jul. 2, 1991, now U.S. Pat. No. 5,192773.

BACKGROUND OF THE INVENTION

Post operative graft rejections are a major complication affecting the success of bone marrow and organ transplantations. However, through the use of immunosuppressive drug therapy, graft rejection in organ transplantation can be significantly reduced.

A wide variety of diseases can be characterized as "autoimmune diseases". Such diseases are similar to graft rejection, except that the rejection is of self tissue. Immunosuppressive therapy can also be of use in preventing this inappropriate self rejection.

One widely accepted immunosuppressant for the prevention of graft rejection is cyclosporin A (CsA). It is a natural product of fungal metabolism and has been demonstrated to have potent immunosuppressive activity in clinical organ transplantations. Calne, R. Y. et al., *Br. Med. J.* 282:934–936 (1981); White, D. J. C. *Drugs* 24:322–334 (1982). Although CsA is widely used in immunosuppressant therapy, its usage (particularly in high dosage) is often accompanied by side effects which include nephrotoxicity, hepatotoxicity and other central nervous system disorders.

The following diseases have been treated with cyclosporin A with positive results, confirming the importance of the autoimmune component in these diseases and their effective treatment with compounds working by selective T-cell immune suppression similar to cyclosporin A.

1) Ophthalmology: Uveitis, Behcet's disease and Grave's ophthalmopathy.

Weetman, A. P. et al., *Lancet* 486–489 (1982). Grave's ophthalmopathy.

Nussenblatt, R. B. et al., *Lancet* 235–238 (1983). Uveitis.

French-Constant, C. et al., *Lancet* 454 (1983). Behcet's disease.

Sanders, M. et al., *Lancet* 454–455 (1983). Behcet's disease.

Note: Cyclosporin A is currently approved in Japan for the treatment of Behcet's disease, the first autoimmune disease indication for this compound.

2) Dermatology: Various autoimmune skin diseases including psoriasis.

Zabel, P. et al., *Lancet* 343 (1984). Acute dermatomyositis.

van Joost, T. et al., *Arch. Dermatol.* 123:166–167 (1987). Atopic skin disease.

Appleboom, T. et al., *Amer. J. Med.* 82:866–867 (1987). Scleroderma.

Logan, R. A. and R. D. R. Camo, *J. Roy. Soc. Med.* 81:417–418 (1988). Eczema.

Griffiths, C. E. M. et al., *Brit. Med. J.* 293:731–732 (1986). Psoriasis.

Ellis, C. N. et al., *J. Amer. Med. Assoc.* 56:3110–3116 (1986). Psoriasis.

3) Hematology: Various diseases including anemia. Toetterman, T. H. et al., *Lancet*, 693 (1984). Pure red cell aplasia (PRCA).

Stryckmans, P. A. et al., *New Engl. J. Med.* 310:655–656 (1984). Aplastic anemia.

Gluckman, E. et al., *Bone Marrow Transplant* 3 Suppl. 1, 241 (1988). Aplasti anemia.

4) Gastroenterology/Hepatology: Primary cirrhosis, autoimmune hepatitis, ulcerative coliris, Crohn's disease and other gastrointestinal autoimmune diseases.

Wiesner, R. H. et al., *Hepatology* 7:1025, Abst. #9, (1987). Primary biliary cirrhosis.

Hyams, J. S. et al., *Gastroenterology* 93:890–893 (1987). Autoimmune hepatitis.

Allison, M. C. et al., *Lancet*, 902–903 (1984). Crohn's disease.

Brynskov, J. et al., *Gastroenterology* 92:1330 (1987). Crohn's disease.

Porro, G. B. et al., *Ital. J. Gastroenterol.* 19:40–41 (1987). Ulcerative colitis.

5) Neurology: Amyotrophic lateral sclerosis (ALS, "Lou Gehrig's disease"), myasthenia gravis and multiple sclerosis.

Appel, S. H. et al., *Arch. Neurol.* 45:381–386 (1988). ALS.

Tindall, R. S. A. et al., *New Engl. J. Med.* 316:719–724 (1987). Myasthenia gravis. *Ann. Neurol.* 24, No. 1, p. 169,m Abstract P174 (1988). Multiple sclerosis.

Dommasch, D. et al., *Neurology* 38 Suppl. 2, 28–29 (1988). Multiple scierosis.

6) Nephrotic Syndrome: Nephrotic syndrome, membrano-proliferative glomerulonephritis (MPGN) and related diseases.

Watzon, A. R. et al., *Clin. Nephrol.* 25:273–274 (1986). Nephrotic syndrome.

Tejani, A. et al., *Kidney Int.* 33:729–734 (1988). Nephrotic syndrome.

Meyrier, A. et al., *Transplat Proc.* 20, Suppl. 4 (Book III), 259–261 (1988). Nephrotic syndrome.

LaGrue, G. et al., *Nephron.* 44:382–382 (1986). MPGN.

7) Rheumatoid Arthritis (RA)

Harper, J. I. et al., *Lancet* 981–982 (1984). RA Van Rijthoven, A. W. et al., *Ann. Rheum. Dis.* 45:726–731 (1986). RA.

Dougados, M. et al., *Ann. Rheum. Dis.* 47:127–133 (1988). RA.

8) Insulin-Dependent Diabetes Mellitus (IDDM) Stiller, C. R. et al., *Science* 223:1362–1367 (1984). IDDM.

Assan, R. et al., *Lancet*, 67–71 (1985). IDDM. Bougneres, P. F. et al., *New Engl. J. Med.* 318:663–670 (1988). IDDM. *Diabetes* 37:1574–1582 (1988). IDDM.

Many veterinary diseases are also characterized as autoimmune diseases. Autoimmune diseases such as those listed above have been observed in mammals. Papa, F. O. et al., *Equine Vet. J.* 22:145–146 (1990) infertility of autoimmune origin in the stallion; Gorman, N. T. and L. L. Werner, *Brit. Vet. J.* 142:403–410, 491–497 and 498–505 (1986) immune mediated diseases of cats and dogs; George, L. W. and S. L. White, *Vet. Clin. North Amer.* 6:203–213 (1984) autoimmune skin diseases in large mammals; Bennett, D., *In. Pract.* 6:74–86 (1984) autoimmune diseases in dogs; Halliwell, R. E., *J. Amer. Vet. Assoc.* 181:1088–1096 (1982) autoimmures diseases in domesticated animals.

The mechanism by which CsA causes immunosuppression has been established. In vitro, CsA inhibits the release

3 of lymphokines, such as interleukin 2 (IL-2) [Bunjes, D. et al., *Eur. J. Immunol.* 11:657–661 (1981)] and prevents clonal expansion of helper and cytotoxic T cells [Larsson, E. *J. Immunol.* 124:2828–2833 (1980)]. CsA has been shown to bind the cytosolic protein, cyclophilin, and inhibit the prolyl-peptidyl cis-trans isomerase (PPIase) activity of that protein. Fischer, G. et al., *Nature* 337:476–478 (1989); Takahashi, N. et al., *Nature* 337:473–475 (1989). The PPIases may mediate T cell activation by catalyzing the rotomerization of peptide bonds of prolyl residues.

Recently, a second natural product isolated from Streptomyces, referred to as FK-506, has been demonstrated to be a potent immunosuppresive agent. Tanaka, H. et al., *J. Am. Chem. Soc.* 109:5031–5033 (1987). FK-506 inhibits IL-2 production, inhibits mixed lymphocyte culture response and inhibits cytotoxic T-cell generation in vitro at 100 times lower concentration than cyclosporin A. Kino, T. et al., *J. Antibiot.* 15:1256– 1265 (1987). FK-506 also inhibits PPIase activity, but is structurally different from CsA and binds to a binding protein (FKBP) distinct from cyclophilin. Harding, M. W. et al., *Nature* 341:758–760 (1989); Siekierka, J. J., *Nature* 341:755–757 (1989).

SUMMARY OF THE INVENTION

This invention relates to a novel class of immunosuppressire compounds having an affinity for the FK-506 binding protein (FKBP). Once bound to this protein, the immunosuppressive compounds inhibit the prolyl peptidyl cis-trans isomerase (rotamass) activity of the FKBP and lead to inhibition of T cell activation. The compounds of this invention can be used as immunosuppressive drugs to prevent or significantly reduce graft rejection in bone marrow and organ transplantations and in the treatment of autoimmune disease in humans and other mammals.

BRIEF DESCRIPTION OF THE FIGURE

FIG. 1 illustrates some preferred compounds of this invention. The synthesis of each of the preferred compounds is described in detail in the Example section.

DETAILED DESCRIPTION OF THE INVENTION

This invention relates to a novel class of immunosuppressire compounds represented by the formula I:

I and pharmaceutically acceptable salts thereof,
wherein A is O, NH, or N-(C1–C4 alkyl);
wherein B is hydrogen, CHL-Ar, (C1–C6)-straight or branched alkyl, (C1–C6)-straight or banched alkenyl, (C5–C7)-cycloalkyl, (C5–C7)-cycloalkenyl or Ar substituted (C1–C6)-alkyl or alkenyl, or

4 wherein L and Q are independently hydrogen, (C1–C6)-straight or branched alkyl or (C1–C6)-straight or branched alkenyl;
wherein T is x or substituted cyclohexyl with substituents at positions 3 and 4 which are independently selected from the group consisting of hydrogen, hydroxyl, O-(C1–C4)-alkyl or O-(C1–C4)-alkenyl and carbonyl;
wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1–C6)-straight or branched alkyl or (C1–C6)-straight or branched alkenyl, O-(C1–C4)-straight or branched alkyl or O-(C1–C4)-straight or branched alkenyl, O-benzyl, O-phenyl, amino and phenyl;
wherein D is either hydrogen or U; E is either oxygen or CH-U, provided that if D is hydrogen, then E is CH-U or if E is oxygen then D is U;
wherein U is hydrogen, O-(C1–C4)-straight or branched alkyl or O-(C1–C4)-straight or branched alkenyl, (C1–C6)-straight or branched alkyl or (C1–C6)-straight or branched alkenyl, (C5–C7)-cycloalkyl or (C5–C7)-cycloalkenyl substituted with (C1–C4)-straight or branched alkyl or (C1–C4)-straight or branched alkenyl, 2-indolyl, 3-indolyl, [(C1–C4)-alkyl or (C1–C4)-alkenyl)]-Ar or Ar (Ar as described above);
wherein J is hydrogen or C1 or C2 alkyl or benzyl; K is (C1–C4)-straight or branched alkyl, benzyl or cyclohexylmethyl; or wherein J and K may be taken together to form a 5–7 membered heterocyclic ring which may contain an oxygen (O), sulfur (S), SO or $SO_2$ substituent therein.

The stereochemistry at position 1 (Formula I) is (R) or (S), with (S) preferred.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, rosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibtyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

Preferably, the compounds will have a molecular weight below about 750 atomic mass units (a.m.u.) and most preferably below about 500 a.m.u. Examples of compounds in which the J and K substituents are taken together to form a heterocyclic ring are shown in Tables 1 and 2. Examples of other preferred compounds of this invention are listed in Tables 3 and 4.

TABLE 1

| No. | B | D | n | $K_i$ | $K_d$ |
|---|---|---|---|---|---|
| 2 | Benzyl | Phenyl | 1 | 25 μM | >5.0 μM |
| 3 | Benzyl | Phenyl | 2 | 1.5 μM | >2.0 μM |
| 4 | Allyl | Phenyl | 2 | 8 μM | ND |
| 5 | 1-Naphthyl | Phenyl | 2 | 0.9 μM | ND |
| 6 | 2-Naphthyl | Phenyl | 2 | 7.0 μM | 1.0 μM |
| 7 | Benzyl | 2-Methylpropyl | 2 | 0.9 μM | ND |
| 8 | Benzyl | 2-Methoxyphenyl | 2 | 17 μM | >75 μM |
| 9 | Benzyl | 3-Methoxyphenyl | 2 | 0.3 μM | >1.3 μM |
| 10 | Benzyl | 4-Methoxyphenyl | 2 | 5.0 μM | 5.0 μM |
| 11 | Benzyl | 3,5-Dimethoxyphenyl | 2 | 2.0 μM | 0.6 μM |
| 12 | Benzyl | 2,6-Dimethoxyphenyl | 2 | 50 μM | 25 μM |
| 13 | Benzyl | 3,4,5-Trimethoxy-phenyl | 2 | 0.1 μM | 2 μM |
| 14 | Benzyl | 4-Fluorophenyl | 2 | 4.0 μM | 10 μM |
| 15 | Benzyl | 3-Nitrophenyl | 2 | 160 μM | >75 μM |
| 16 | Benzyl | 4-Nitrophenyl | 2 | 160 μM | 100 μM |
| 17 | Benzyl | 2-Pyridyl | 2 | 130 μM | >1000 μM |
| 18 | Benzyl | 2-Pyridyl-N-oxide | 2 | >500 μM | 10 μM |
| 19 | tert-Butyl | 2-Furyl | 1 | 200 μM | >500 μM |
| 20 | Benzyl | 2-Furyl | 2 | 3 μM | >12 μM |
| 21 | Benzyl | 3-Indolyl | 2 | 25 μM | 20 μM |
| 22 | Benzyl | 2-Thiophenyl | 2 | 0.8 μM | 4 μM |
| 23 | E-3-Phenyl-2-methyl-prop-2-enyl | Phenyl | 2 | 1.5 μM | ND |
| 24 | E-3-(4-Hydroxy-phenyl)-2-methyl-prop-2-enyl | Phenyl | 2 | 6 μM | ND |
| 25 | E-3-[cis-(4-hydroxycyclo-hexyl)]-2-methyl-prop-2-enyl | Phenyl | 2 | 0.6 μM | ND |
| 26 | E-3-[trans-(4-Hydroxycyclo-hexyl)]-2-methyl-prop-2-enyl | Phenyl | 2 | 0.5 μM | ND |
| 27 | Benzyl | 2-Nitrobenzyl | 1 | 26 μM | >25 μM |
| 28 | Hydrogen | Methoxy | 2 | ND | ND |
| 29 | tert-Butyl | Methoxy | 1 | 600 μM | >500 μM |
| 30 | Allyl | Methoxy | 2 | 190 μM | >25 μM |
| 31 | Benzyl | Methoxy | 2 | 80 μM | >50 μM |
| 32 | 2-Cyclohexylethyl | Methoxy | 2 | 45 μM | >40 μM |
| 33 | 3-Cyclohexylpropyl | Methoxy | 2 | 20 μM | 12 μM |
| 34 | 4-Cyclohexylbutyl | Methoxy | 2 | 6 μM | 2–3 μM |
| 35 | Cyclopentyl-propyl | Methoxy | 2 | 35 μM | ND |
| 36 | E-3-(4-Methoxy-phenyl)-2-methyl-prop-2-enyl | Methoxy | 2 | 40 μM | >30 μM |
| 37 | E-3-(3,4-Dime-thoxyphenyl)-2-methyl-prop-2-enyl | Methoxy | 2 | 10 μM | ND |
| 38 | E-3-(4-Hydroxy-phenyl)-2-methyl-prop-2-enyl | Methoxy | 2 | 60 μM | ND |

TABLE 1-continued

| No. | B | D | n | Ki | $K_d$ |
|---|---|---|---|---|---|
| 39 | E-3-[cis-(4-Hydroxycyclohexyl)]-2-methyl-prop-2-enyl | Methoxy | 2 | 70 μM | >20 μM |
| 40 | Benzyl | Cyclohexyl | 2 | 1.3 μM | 3 μM |
| 41 | Benzyl | Ethyl | 1 | 400 μM | >300 μM |
| 42 | Benzyl | 3-Methoxyphenyl | 1 | 5 μM | 80 μM |
| 43 | Benzyl | 2-Pyridyl | 1 | 300 μM | ND |
| 44 | Benzyl | 3,4-Difluorophenyl | 2 | 3 μM | ND |
| 45 | Benzyl | (E)-2-(4-Methoxyphenyl)-ethenyl | 2 | 1 μM | ND |
| 46 | Benzyl | 1-Hydroxy-1-cyclohexyl | 2 | 1 μM | 2 μM |
| 47 | Benzyl | 2-Naphthyl | 2 | 1.5 μM | 0.3 μM |
| 48 | Benzyl | 1-Naphthyl | 2 | 1 μM | 2 μM |
| 49 | (S)-α-Methylbenzyl | Phenyl | 2 | 0.5 μM | 0.6 μM |
| 50 | Benzyl | 2-Hydroxy-2-tetrahydropyranyl | 2 | 12 μM | 0.35 μM |
| 51 | (R)-α-Methylbenzyl | Phenyl | 2 | 1.5 μM | 1 μM |
| 52 | Benzyl | 3-Trifluoromethylphenyl | 2 | 1.5 μM | 1.3 μM |
| 53 | Benzyl | 3-Benzyloxyphenyl | 2 | 0.5 μM | 0.2 μM |
| 54 | Benzyl | (E)-2-tert-Butylethenyl | 2 | 9 μM | 3 μM |
| 55 | Benzyl | 2-Trifluoromethylphenyl | 2 | 5 μM | ND |
| 56 | 4-Cyclohexylbutyl | Phenyl | 2 | 0.4 μM | ND |
| 57 | 4-Cyclohexylbutyl | 3,4,5-Trimethoxyphenyl | 2 | 0.04 μM | 0.1 μM |
| 58 | 4-Phenylbenzyl | Phenyl | 2 | 5 μM | ND |
| 59 | 4-Phenylbenzyl | 3,4,5-Trimethoxyphenyl | 2 | 2 μM | ND |
| 60 | Benzyl | 3-Ethoxyphenyl | 2 | 0.56 μM | ND |
| 61 | 3-Phenoxybenzyl | 3,4,5-Trimethoxyphenyl | 2 | 0.018 μM | 0.035 μM |
| 62 | 3-Phenoxybenzyl | Phenyl | 2 | 0.09 μM | 0.15 μM |
| 63 | 4-Phenylbutyl | 3,4,5-Trimethoxyphenyl | 2 | 0.019 μM | 0.1 μM |
| 64 | 4-Phenylbutyl | Phenyl | 2 | 0.35 μM | ND |
| 65 | Benzyl | 3-(3-Propenyloxy)phenyl | 2 | 1 μM | ND |
| 66 | Benzyl | 3-(2-Propoxy)phenyl | 2 | 0.5 μM | ND |
| 67 | Benzyl | 1-Methylpropyl | 2 | 1 μM | ND |
| 68 | 2-Phenylethyl | Phenyl | 2 | 1.1 μM | ND |
| 69 | 6-Phenylhexyl | Phenyl | 2 | 0.5 μM | ND |
| 70 | 5-Phenylpentyl | 3,4,5-Trimethoxyphenyl | 2 | 0.07 μM | ND |
| 71 | 6-Phenylhexyl | 3,4,5-Trimethoxyphenyl | 2 | 0.1 μM | 0.05 μM |
| 72 | 6-Cyclohexylhexyl | 3,4,5-Trimethoxyphenyl | 2 | 0.05 μM | 0.5 μM |
| 73 | 4-Phenoxybenzyl | 3,4,5-Trimethoxyphenyl | 2 | 0.8 μM | ND |
| 74 | 5-Cyclohexylpentyl | 3,4,5-Trimethoxyphenyl | 2 | 0.09 μM | 0.08 μM |
| 75 | Benzyl | 3-(1-Butoxy)phenyl | 2 | 0.36 μM | ND |
| 76 | 4-Phenylbutyl | 3-(2-Propoxy)phenyl | 2 | 0.1 μM | ND |
| 77 | 4-(4-Iodophenyl)butyl | 3,4,5-Trimethoxyphenyl | 2 | 0.016 μM | 0.06 μM |
| 78 | 4-Iodobenzyl | 3,4,5-Trimethoxyphenyl | 2 | 1.4 μM | ND |
| 79 | 2-(2-Naphthyl)ethyl | 3,4,5-Trimethoxyphenyl | 2 | 0.22 μM | ND |
| 80 | 2-(1-Naphthyl)ethyl | 3,4,5-Trimethoxyphenyl | 2 | 0.5 μM | ND |
| 81 | 4-Phenylbutyl | 4-Iodophenyl | 2 | 0.8 μM | 0.25 μM |
| 82 | 4-Phenylbutyl | 3-Iodophenyl | 2 | 0.13 μM | 0.2 μM |
| 83 | 3-Phenylpropyl | 3,4,5-Trimethoxyphenyl | 2 | 0.11 μM | ND |
| 84 | 3-(3-Indolyl)propyl | 3,4,5-Trimethoxyphenyl | 2 | 0.017 μM | 0.054 μM |
| 85 | 4-(4-Methoxyphenyl)butyl | 3,4,5-Trimethoxyphenyl | 2 | 0.013 μM | 0.049 μM |
| 86 | 4-Phenylbut-2-enyl | 3,4,5-Trimethoxyphenyl | 2 | 0.8 μM | ND |
| 87 | 4-Phenylbut-3-enyl | 3,4,5-Trimethoxyphenyl | 2 | 0.5 μM | ND |
| 88 | 4-(4-Allocaminophenyl)propyl | 3,4,5-Trimethoxyphenyl | 2 | 0.011 μM | 0.07 μM |
| 89 | 4-Phenylpropyl | 1-Cyclohexenyl | 2 | 0.78 μM | ND |
| 90 | 4-(4-Methoxyphenyl)but-3-enyl | 3,4,5-Trimethoxyphenyl | 2 | 0.011 μM | 0.60 μM |
| 91 | 4-Phenylpropyl | 1-Fluoro-1-cyclohexyl | 2 | 0.54 μM | ND |
| 92 | 4-Phenylpropyl | 3-Butoxyphenyl | 2 | 1.4 μM | ND |
| 93 | 3-[3-(N-Formlindolyl)propyl | 3,4,5-Trimethoxyphenyl | 2 | 0.015 μM | 0.06 μM |
| 94 | 4-(3-Indolyl)butyl | 3,4,5-Trimethoxyphenyl | 2 | 0.016 μM | 0.05 μM |
| 95 | 4-Phenylbutyl | Benzyl | 2 | 0.35 μM | ND |
| 96 | 4-Phenylbutyl | 3-Biphenyl | 2 | 0.04 μM | 0.033 μM |
| 97 | 4-Phenylbutyl | 4-tert-Butylphenyl | 2 | 0.6 μM | ND |
| 98 | 4-Phenylbutyl | Cyclohexyl | 2 | 0.08 μM | 0.18 μM |
| 99 | 4-Phenylbutyl | Cyclohexylmethyl | 2 | 0.12 μM | ND |
| 100 | 4-Phenylbutyl | 3,4-Methylenedioxyphenyl | 2 | 0.25 μM | ND |

TABLE 1-continued

| No. | B | D | n | Ki | $K_d$ |
|---|---|---|---|---|---|
| 101 | 4-Phenylbutyl | 4-Tetrahydropyranyl | 2 | 0.44 μM | ND |
| 102 | 4-Phenylbutyl | 3-Cyclohexyl-4-methoxyphenyl | 2 | 14 μM | ND |
| 103 | 4-Phenylbutyl | 4-(4-Methoxybenzyloxymethyl)-2-furyl | 2 | 0.7 μM | ND |
| 104 | 4-Phenylbutyl | tert-Butyl | 2 | 0.18 μM | ND |
| 105 | 4-Phenylbutyl | Ethyl | 2 | 1.6 μM | ND |
| 106 | 3-(N-Benzimidazolyl)propyl | 3,4,5-Trimethoxyphenyl | 2 | 0.11 μM | ND |
| 107 | 3-(N-Purinyl)propyl | 3,4,5-Trimethoxyphenyl | 2 | 0.13 μM | ND |
| 108 | (S,S)-2-Methyl-3-hydroxy-4-phenylpropyl | 3,4,5-Trimethoxyphenyl | 2 | 0.25 μM | ND |

ND Indicates not determined.

TABLE 2

| No. | B | U | n | Ki | $K_d$ |
|---|---|---|---|---|---|
| 109 | Benzyl | 3,4-Methylenedioxyphenyl | 1 | 3 μM | >15 μM |
| 110 | Benzyl | 3,4-Methylenedioxyphenyl | 2 | 3 μM | >4 μM |
| 111 | Benzyl | 4-Methoxyphenyl | 1 | 6 μM | >30 μM |
| 112 | Benzyl | 4-Methoxyphenyl | 2 | 4 μM | >8 μM |
| 113 | Benzyl | 2,5-Dimethoxyphenyl | 1 | 10 μM | ND |
| 114 | Benzyl | 2,4,5-Trimethoxyphenyl | 1 | 25 μM | ND |
| 115 | Benzyl | 3,4,5-Trimethoxyphenyl | 1 | 450 μM | >25 μM |
| 116 | Benzyl | 4-Dimethylaminophenyl | 2 | 20 μM | >5 μM |

TABLE 2-continued

| No. | B | U | n | Ki | $K_d$ |
|---|---|---|---|---|---|
| 117 | Benzyl | 4-Nitrophenyl | 2 | 14 μM | >5 μM |
| 118 | Benzyl | 2-Furyl | 2 | 2.5 μM | ND |
| 119 | Benzyl | 3-Furyl | 2 | 2.5 μM | ND |
| 120 | Benzyl | 3-Indolyl | 2 | >60 μM | >8 μM |
| 121 | Benzyl | 3-Pyridyl | 2 | 25 μM | ND |
| 122 | Benzyl | Hydrogen | 2 | 300 μM | ND |
| 123 | Benzyl | Phenyl | 2 | 11 μM | ND |

TABLE 3

| No | B | D | J | K | Ki | $K_d$ |
|---|---|---|---|---|---|---|
| 124 | Benzyl | Methoxy | Methyl | Hydrogen | 1000 μM | >200 μM |
| 125 | Benzyl | Methoxy | Methyl | S-Methyl | 400 μM | >200 μM |
| 126 | Benzyl | Methoxy | Methyl | S-Isopropyl | 170 μM | >200 μM |
| 127 | Ethyl | Methoxy | Benzyl | Hydrogen | >1200 μM | >300 μM |
| 128 | tert-Butyl | Methoxy | Ethyl | S-Methyl | >400 μM | >500 μM |

TABLE 4

| No | B | U | J | K | Ki | $K_d$ |
|---|---|---|---|---|---|---|
| 129 | Benzyl | 4-Methoxyphenyl | Methyl | S-Methyl | 80 μM | >150 μM |
| 130 | Benzyl | 4-Methoxyphenyl | Methyl | S-Isopropyl | 30 μM | >20 μM |
| 131 | Benzyl | 3,4-Methylenedioxyphenyl | Methyl | S-Methyl | 50 μM | ND |
| 132 | Benzyl | 3,4-Methylenedioxyphenyl | Hydrogen | S-Methyl | 60 μM | ND |

The immunosuppressive compounds of this invention have an affinity for the FK-506 binding protein which is located in the cytosol of lymphocytes, particularly T lymphocytes. When the imunosuppreseive compounds are bound to the FKBP, they act to inhibit the prolylpeptidyl cis-trans isomerase activity of the binding protein and inhibit lymphocyte activation mediated by FKBP. One particular FK-506 binding protein has been identified by Harding, M. W. et al., Nature 341:758–760 (1989) and can be used as the standard by which to evaluate binding affinity of the compounds for FKBP. Compounds of this invention, however, may have an affinity for other FK-506 binding proteins. Inhibition of the prolyl peptidyl cis-trans isomerase may further be indicative of binding to an FK-506 binding protein.

Human FK-506 binding protein can be obtained as described by Harding, M. W. et al., Nature 341:758–760 (1989). Values for the apparent $K_d$ can be determined from a competitive LH-20 binding assay performed as described by Harding et al., using 32-[1-$^{14}$C]-benzoyl FK-506 as a reporting ligand; or using [$^3$H]dihydro-FK-506, as described by Siekierka, J. J. et al., Nature 341:755–757 (1989). The binding affinities for several compounds of this invention for the FKBP are reported in Tables 1–4. The data was obtained using the latter method, where the ability of an unlabeled compound to compete with the binding of [$^3$H]dihydro-FK-506 to FK-506 binding protein was measured.

The inhibition of the PPIase (rotamase) enzyme activity of the FKBP (apparent "Ki" values) can also be measured according to the methods described by either Harding, M. W. et al., Nature 341:758–760 (1989) or Siekierka, J. J. et al., Nature 341:755–757 (1989). The cis-trans isomerization of the proline-alanine peptide bond in a model substrate, N-succinylAla-Ala-Pro-Phe-p-nitroanilide, is monitored spectrophotometrically in a coupled assay with chymotrypsin, which releases 4-nitroanilide from the trans form of the substrate. Fischer, G. et al., Nature 337:476–478 (1989). The inhibitory effect of the addition of different concentrations of inhibitor on the extent of the reaction is determined, and analysis of the change in first order rate constant as a function of inhibitor concentration yields an estimate of the apparent Ki value. The extent of enzyme inhibition ($K_i$) of some preferred compounds is shown in Tables 1–4.

The compounds of the present invention can be further characterized in cellular biological experiments in vitro where their resemblance in function and use to cyclosporin A and to FK-506 is apparent. (See Tables 5 and 6)

TABLE 5

| Assays and $IC_{50}$ Value for Drugs | Cyclosporin A | Rapamycin | FK-506 |
|---|---|---|---|
| 1) Human PBL + OKT3 | <1 μg/ml | <1 μg/ml | <1 μg/ml |
| 2) T-Cell Hybridoma + TCR/CD2 | <1 μg/ml | <1 μg/ml | <1 μg/ml |
| 3) Apoptosis | Blocks at 1 μg/ml | Inactive at 1 μg/ml | Blocks at 1 μg/ml |
| 4) CTLL Proliferation + IL-2 | >>1 μg/ml | ≈0.01 μg/ml | >>1 μg/ml |

TABLE 6

Cellular Assay Results

| No. | PMA (μM) | OKT3 (μM) | LB (μM) | JVM (μM) | CTLL (μM) |
|---|---|---|---|---|---|
| 2 | ND | ND | ND | ND | ND |
| 3 | 7.6 | 4.6 | >10 | >10 | >8.5 |
| 4 | ND | ND | ND | ND | ND |
| 5 | >10 | >10 | >10 | >10 | >10 |
| 6 | ND | ND | ND | ND | ND |
| 7 | >10 | >10 | >10 | >10 | >10 |
| 8 | ND | ND | ND | ND | ND |
| 9 | >10 | 6.5 | >10 | >10 | >10 |
| 10 | ND | ND | ND | ND | ND |
| 11 | ND | ND | ND | ND | ND |
| 12 | ND | ND | ND | ND | ND |
| 13 | >10 | 5.9 | >10 | >10 | >10 |
| 14 | ND | ND | ND | ND | ND |
| 15 | ND | ND | ND | ND | ND |
| 16 | >10 | >10 | >10 | >10 | >10 |
| 17 | ND | ND | ND | ND | ND |
| 18 | ND | ND | ND | ND | ND |
| 19 | ND | ND | ND | ND | ND |
| 20 | ND | ND | ND | ND | ND |
| 21 | ND | ND | ND | ND | ND |
| 22 | >10 | >10 | >10 | >10 | >10 |
| 23 | >10 | >10 | >10 | >10 | >10 |
| 24 | ND | ND | ND | ND | ND |
| 25 | >10 | >10 | >10 | >10 | >10 |
| 25 | >10 | >10 | >10 | >10 | >10 |
| 26 | >10 | 6.5 | >10 | >10 | >10 |
| 27 | ND | ND | ND | ND | ND |

TABLE 6-continued

Cellular Assay Results

| No. | PMA (μM) | OKT3 (μM) | LB (μM) | JVM (μM) | CTLL (μM) |
|---|---|---|---|---|---|
| 28 | ND | ND | ND | ND | ND |
| 29 | ND | ND | ND | ND | ND |
| 30 | ND | ND | ND | ND | ND |
| 31 | ND | ND | ND | ND | ND |
| 32 | ND | ND | ND | ND | ND |
| 33 | ND | ND | ND | ND | ND |
| 34 | ND | ND | ND | ND | ND |
| 35 | ND | ND | ND | ND | ND |
| 36 | ND | ND | ND | ND | ND |
| 37 | ND | ND | ND | ND | ND |
| 38 | ND | ND | ND | ND | ND |
| 39 | ND | ND | ND | ND | ND |
| 40 | 7.0 | 1.0 | >10 | >10 | >10 |
| 41 | ND | ND | ND | ND | ND |
| 42 | ND | ND | ND | ND | ND |
| 43 | ND | ND | ND | ND | ND |
| 44 | ND | ND | ND | ND | ND |
| 45 | >10 | >10 | >10 | >10 | >10 |
| 46 | >10 | >10 | >10 | >10 | >10 |
| 47 | >10 | >10 | >10 | >10 | >10 |
| 48 | >10 | >10 | >10 | >10 | >10 |
| 49 | >10 | 6.2 | >10 | >10 | >10 |
| 50 | ND | ND | ND | ND | ND |
| 51 | ND | ND | ND | ND | ND |
| 52 | >10 | >10 | >10 | >10 | >10 |
| 53 | >10 | 8.0 | >10 | >10 | 8.0 |
| 54 | ND | ND | ND | ND | ND |
| 55 | ND | ND | ND | ND | ND |
| 56 | >10 | >10 | >10 | 6.5 | 5.0 |
| 57 | 4.0 | 4.5 | >10 | 8.0 | 6.0 |
| 58 | ND | ND | ND | ND | ND |
| 59 | ND | ND | ND | ND | ND |
| 60 | >10 | >10 | >10 | >10 | >10 |
| 61 | 4.0 | 8.0 | >10 | >10 | 3.2 |
| 62 | 6.5 | >10 | >10 | >10 | >10 |
| 63 | 6.0 | 3.1 | 10 | 8.5 | 3.8 |
| 64 | 10 | 6.0 | >10 | >10 | >10 |
| 65 | >10 | >10 | >10 | >10 | >10 |
| 66 | >10 | >10 | >10 | >10 | >10 |
| 67 | >10 | >10 | >10 | >10 | >10 |
| 68 | >10 | >10 | >10 | >10 | >10 |
| 69 | 6.1 | >10 | >10 | >10 | >10 |
| 70 | 7.0 | 4.5 | >10 | 9.0 | 4.2 |
| 71 | 5.0 | 5.5 | 7.5 | 8.0 | 3.8 |
| 72 | 9.0 | >10 | >10 | >10 | 5.5 |
| 73 | 8.0 | >10 | 4.5 | 6.0 | 7.0 |
| 74 | 8.0 | 9.0 | 10 | 10 | 5.0 |
| 75 | 8.0 | >10 | 9.0 | >10 | 4.5 |
| 76 | 5.0 | 10 | 9.0 | >10 | 6.0 |
| 77 | 4.5 | 8.0 | 6.0 | 7.0 | 2.1 |
| 78 | >10 | >10 | >10 | >10 | >10 |
| 79 | 10 | 2.5 | >10 | >10 | 8.0 |
| 80 | 3.0 | 4.0 | 10 | 10 | 6.0 |
| 81 | 7.0 | >10 | >10 | >10 | >10 |
| 82 | 10 | >10 | >10 | >10 | >10 |
| 83 | 5.5 | 5.5 | 8.5 | 7.5 | 5.0 |
| 84 | 4.5 | 6.0 | 6.0 | >10 | 2.0 |
| 85 | 4.5 | 4.5 | 7.0 | 10 | 1.5 |
| 86 | 9.0 | >10 | >10 | >10 | >10 |
| 87 | 7.0 | >10 | >10 | >10 | >10 |
| 88 | 2.2 | 2.2 | 2.5 | 4.5 | 4.0 |
| 89 | 8.0 | >10 | >10 | >10 | >10 |
| 90 | 8.0 | >10 | >10 | >10 | 7.0 |
| 91 | >10 | >10 | >10 | >10 | >10 |
| 92 | 9.0 | >10 | >10 | >10 | >10 |
| 93 | 6.0 | 7.0 | 10 | 8.7 | 3.7 |
| 94 | 5.0 | 5.5 | >10 | 7.0 | 4.0 |
| 95 | >10 | >10 | >10 | >10 | >10 |
| 96 | >10 | >10 | >10 | >10 | >10 |
| 97 | >10 | >10 | >10 | >10 | 6.0 |
| 98 | >10 | >10 | >10 | >10 | >10 |
| 99 | >10 | >10 | >10 | >10 | >10 |
| 100 | >10 | >10 | >10 | >10 | >10 |
| 101 | >10 | >10 | >10 | >10 | >10 |
| 102 | >10 | >10 | 10 | 10 | >10 |
| 103 | 7.0 | 10 | 10 | >10 | 10 |
| 104 | 4.0 | >10 | >10 | >10 | >10 |
| 105 | >10 | >10 | >10 | >10 | >10 |
| 106 | 7.0 | >10 | >10 | >10 | 3.0 |
| 107 | 6.5 | >10 | >10 | >10 | >10 |
| 108 | >10 | >10 | 8.0 | >10 | >10 |
| 109 | ND | ND | ND | ND | ND |
| 110 | ND | ND | ND | ND | ND |
| 111 | ND | ND | ND | ND | ND |
| 112 | ND | ND | ND | ND | ND |
| 113 | ND | ND | ND | ND | ND |
| 114 | ND | ND | ND | ND | ND |
| 115 | ND | ND | ND | ND | ND |
| 116 | ND | ND | ND | ND | ND |
| 117 | ND | ND | ND | ND | ND |
| 118 | ND | ND | ND | ND | ND |
| 119 | ND | ND | ND | ND | ND |
| 120 | ND | ND | ND | ND | ND |
| 121 | ND | ND | ND | ND | ND |
| 122 | ND | ND | ND | ND | ND |
| 123 | ND | ND | ND | ND | ND |
| 124 | ND | ND | ND | ND | ND |
| 125 | ND | ND | ND | ND | ND |
| 126 | ND | ND | ND | ND | ND |
| 127 | ND | ND | ND | ND. | ND |
| 128 | ND | ND | ND | ND | ND |
| 129 | ND | ND | ND | ND | ND |
| 130 | ND | ND | ND | ND | ND |
| 131 | ND | ND | ND | ND | ND |
| 132 | ND | ND | ND | ND | ND |

All of the compounds in Table 6 showed toxicity at higher concentrations than their immunosuppresive activity and were typically concentrations >10 μM.
PMA and OKT3-mitogens used to stimulate proliferation of human peripheral blood lymphocytes (PBC). Compounds are evaluated on their ability to inhibit proliferation.
LB and JVM-human viral-transformed B lymphoblastoid cell lines stimulated to proliferate in a mixed lymphocyte reaction (MLR). The compounds are evaluated on their ability to inhibit this proliferation.
CTLL-inhibition of proliferation of cytotoxic T cells stimulated by IL-2.

1) Assay similar to Yoshimura, N. et al., *Transplantation* 47:356–359 (1989). Assay uses fresh human peripheral blood lymphocytes isolated by Ficoll-Hypaque density centrifugation, stimulated bythe OKT3 antibody (anti-CD3) which stimulates via interaction with CD3. Stimulation is measured by incorporation of radioactive thymidine [($^3$H)TdR] into proliferating cells, with an uninhibited control signal of 48,000–75,000 cpm. $IC_{50}$ values are estimated from inhibitions of proliferation observed at various drug concentrations.

2) Assay similar to above, but using T-cell clone stimulated with antibody to the T-cell receptor (TCR) and antibody to CD2. Stimulation is measured by incorporation of radioactive thymidine [($^3$H)TdR] into proliferating cells, with an uninhibited control signal of 23,000 cpm. $IC_{50}$ values are estimated from inhibitions of proliferation observed at various drug concentrations.

3) Assay according to Shi, Y. et al., *Nature* 339:625–626 (1989). The assay uses a T-cell hybridoma similar to that described. The assay measures activation-induced (anti-CD3) cell death (evaluated by counting viable cells after staining as described) in a T-cell hybridoma that mimics the effect known to occur in immature thymocytes. The ability of cyclosporin A and FK-506 to inhibit this cell death is herein used as a sensitive indication of compounds with cyclosporin-like and/or FK-506-like mechanism of action. Note that the chemically related, but mecanistically distinct, immunosuppressant rapamycin is inactive in this assay.

4) Assay according to DuMont, F. et al., *J. Immunol.* 144:251–258 (1990). The assay measures the stimulation of CTLL cells in response to IL-2. Proliferation is measured by incorpoation of ($^3$H)TdR. Imunosuppressants which work by a similar mechanism to cyclosporin A and FK-506 will not inhibit in this IL-2 driven process, since they function by the inhibition of production of endogenous IL-2. In this assay, exogenous IL-2 is provided to overcome this block. Note that the chemically related, but mechanistically distinct immunosuppressant, rapamycin, is active in this assay.

These assays can be used to profile the cellular activity of the compounds of the present invention. Thus, it is clear from these results that the compounds resemble both cyclosporin A and FK-506 in its cellular activity, including immunosuppression, in contrast to the mechanistically dissimilar immunosuppressant agent rapamycin. Furthermore, the observed cellular activity is consistent quantitatively with the activity observed for FKBP binding and inhibition of PPIase (rotamass) activity shown in Table 1.

Thus, the compounds can be used as immunosuppressants for prophylaxis of organ rejection or treatment of chronic graft rejection and for the treatment of autoimmune diseases.

The immunosuppresstve compounds of this invention can be periodically administered to a patient undergoing bone marrow or organ transplantation or for another reason in which it is desirable to substantially reduce or suppress a patient's immune response, such as in various autoimmune diseases. The compounds of this invention can also be administered to mammals other than humans for treatment of various mammalian autoimmune diseases.

The novel compounds of the present invention possess an excellent degree of activity in suppression of antigen-stimulated growth and clonal expansion of T-cells, especially those T-cells characterized as "helper" T-cells. This activity is useful in the primary prevention of organ transplant rejection, in the rescue of transplanted organs during a rejection episode, and in the treatment of any of several autoimmune diseases known to be associated with inappropriate autoimmune responses. These autoimmune diseases include: uveitis, Behcet's disease, Graves ophthalmopathy, psoriasis, acute dermatomyositis, atopic skin disease, scleroderma, eczema, pure red cell aplasia, aplastic anemia, primary cirrhosis, autoimmune hepatitis, ulcerative colirhosis, Crohn's disease, amyotrophic lateral sclerosis, myasthenia gravis, multiple sclerosis, nephrotic syndrome, membranoproliferative glomerulonephritis, rheumatoid arthritis and insulin-dependent diabetes mellitus. In all of the above-listed autoimmune diseases, treatment is effective to reduce the symptoms and slow progression of the disease. In the case of insulin-dependent diabetes mellitus, treatment as described below is most effective when instituted before the complete cessation of natural insulin production and transition to complete dependence on external insulin.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvnts and vehicles. The term parenteral as used herein includes subcutaneous, intravenous, intramuscular, intrasternal and intracranial injection or infusion techniques.

The pharmaceutical compositions may be in the form of a sterile injectable preparation, for example as a sterile injectible aqueous or oleagenous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. Fatty acids such as oleic acid and its glyceride derivatives find use in the preparation of injectables, as do natural pharmaceutically-acceptable oils, such as olive oil or castor oil, especially in their polyoxyethylated versions. These oil solutions or suspensions may also contain a long-chain alcohol diluent or dispersant such as Ph. Helv or similar alcohol.

The compounds may be administered orally, in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at the rectal temperature and therefore will melt in the rectum to release the drug. Such materials include cocoa butter, beeswax and polyethylene glycols.

The compounds of this invention may also be administered topically, especially when the conditions addressed for treatment involve areas or organs readily accessible by topical application, including autoimmune diseases of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses, the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation.

Dosage levels on the order of 0.01 to 100 mg/kg per day of the active ingredient compound are useful in the treatment of the above conditions. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed, the age, body weight, general health, sex, diet, time of administration, rate of excretion, drug combination and the severity of the particular disease being treated.

The compound can also be administered in combination with asteroid, such as methyl prednisalone acetate, for additional immunosuppressive effect. The steroid is administered orally, intravenously, rectally, topically or by inhalation. Dosages (based upon methyl prednisalone acetate) of 0.1–5 mg/kg/day may be employed. An initial loading dose of 100–500 mg may be employed. Steroid doses may be decreased with time from the higher toward the lower doses as the clinical situation indicates.

The compounds can be administered with other immunosuppressant drugs, such as rapamyctn, azathioprine, 15-deoxyspergualin, cyclosporin, FK-506 or combinations of these, to increase the immunosuppressive effect. Administration of cyclosporin and FK-506 together should be avoided due to contraindications reported resulting from coadministration of these immunosuppressants. The dosage level of other immunosuppressant drugs will depend upon the factors previously stated and the immunosuppressive effectiveness of the drug combination.

OKT3, which is a murine monoclonal antibody to CD3 surface antigen of human T lymphocytes, can also be coadministered intravenously with compounds of the present inventions for rescue and reversal of acute allograft rejections, particularly in renal transplantations.

The invention will be further illustrated by way of the following examples, which are not intended to be limiting in any way.

EXAMPLES

General

Proton nuclear magnetic resonance ($^1$H NMR) spectra were recorded at 300 MHz on a Bruker AC 300 or at 500 MHz on a Bruker AMX 500. Chemical shifts for proton resonances are reported in parts per million ($\delta$) relative to Me$_4$Si ($\delta 0.0$). Analytical high performance liquid chromatography (HPLC) was performed on either a Waters 600 E or a Hewlett Packard 1050 liquid chromatograph. HPLC assessments of compounds were run on a Waters Associates Delta Pak 5 micron, 15 cm. column at a flow rate of 1.5 mL per minute. The solvent system used was: A=0.1% H$_3$PO$_4$/H$_2$O; B=0.1% H$_3$PO$_4$/CH$_3$CN. A linear gradient of 95% A/5% B to 100% B over 15 minutes followed by 1.5 minutes at 100% B was used, with detection at 214 nM.

Figure 1A:
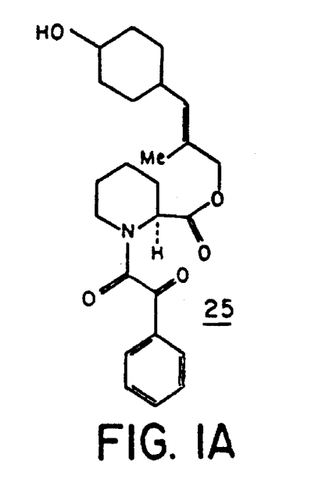
Figure 1B:
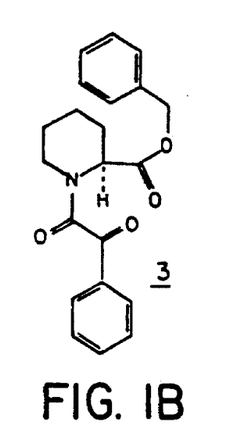
Figure 1C:
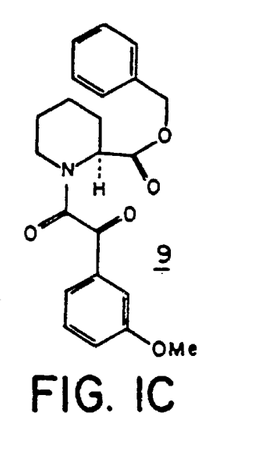
Figure 1D:
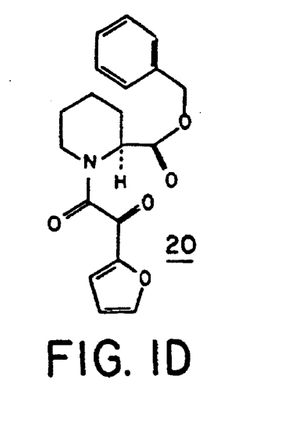
Figure 1E:
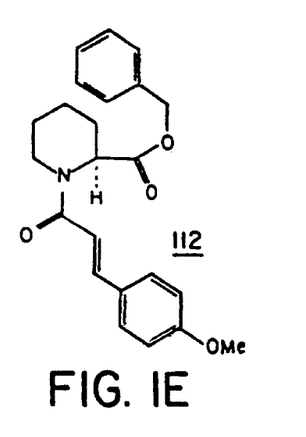
Figure 1F:
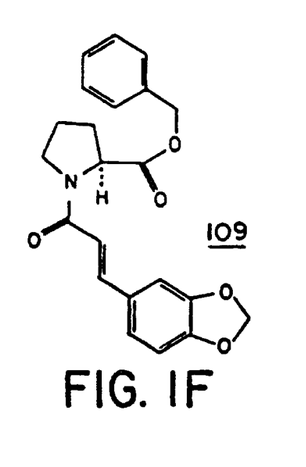
Figure 1G:
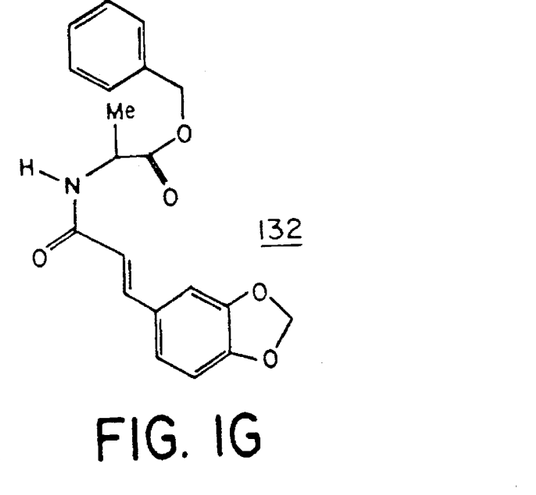
Figure 1H:
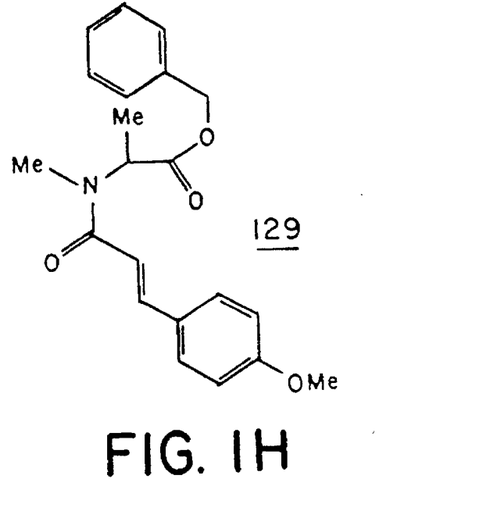
Figure 1I:
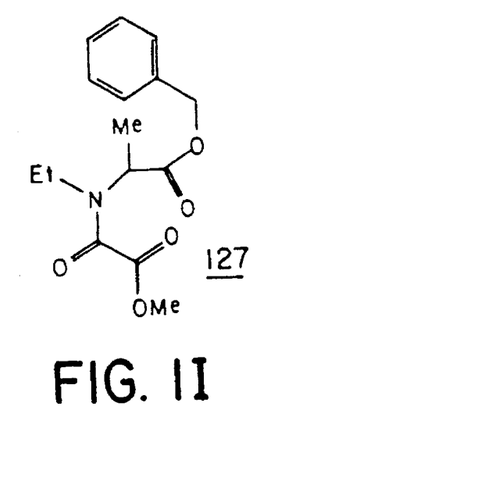
Figure 1J:
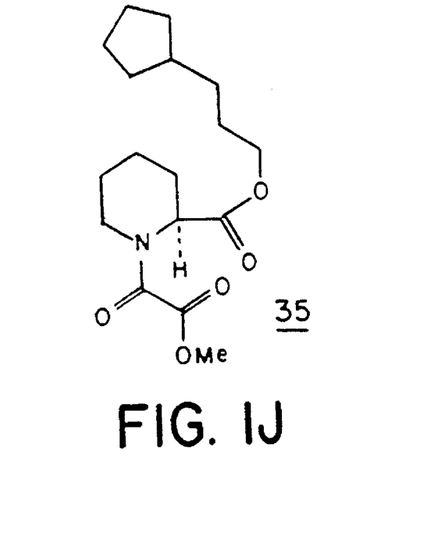

The compounds described below are illustrated in FIG. 1.

EXAMPLE 1

Synthesis of (E)-3-[cis-4-(hydroxycyclohexyl)]-2-methylprop-2-enyl N-(phenylglyoxyl)-pipecolate (25)

1. (S)-Benzyl Pipecolate (133)

To a slurry of 7.3 g (26.14 mmol) of the tartrate salt of (S)-pipecolic acid (Egbertson M. and S. J. Danishefsky, *J. Org. Chem.* 54:11 (1989) in 75 mL of dry benzene was added 13.5 mL (0.13 mol) of benzyl alcohol and 5.48 g (28.8 mmol) of p-toluenesulfonic acid monohydrate. The reaction mixture was heated at reflux under a Dean-Stark trap for 2 h and then cooled to room temperature. The solution was then diluted with 400 mL of ether and stirred overnight at 4° C. The resulting white solid was collected on a filter, washed with hexane and dried in vacuo to give 9.2 g (90%) of the p-toluenesulfonic acid salt of benzyl pipecolate (134). $^1$H NMR (300 MHz, D$_2$O) $\delta$7.63 (d), 7.41 (s), 7.28 (d), 5.26 (ABq), 4.8 (s), 4.03 (dd), 3.92 (dd), 3.51–3.39 (m), 3.15–2.93 (s), 2.40 (s), 2.36–2.24 (m), 1.98–1.53 (m).

Benzyl pipecolate was routinely generated by treating an ethyl acetate suspension of this salt with saturated sodium bicarbonate until dissolution of the organic material. The aqueous layer was extracted twice with ethyl acetate and the combined organic extracts were dried with MgSO$_4$ and evaporated to yield (S)-Benzyl pipecolate (133) as a pale yellow oil.

2. (S)-N-(Phenylglyoxyl)pipecolic Acid (135)

To a solution of 4.95 g (17.72 mmol) of the tartrate salt of L-(S)-pipecolic acid in 18.0 mL of methylene chloride at 0° C. was added 20.4 mL (117.10 mmol) of diisopropylethylamine followed by 12.4 mL (97.7 mmol) of chlorotrimethylsilane and the resulting solution was stirred at 0° C. for 15 minutes. To this mixture was added 17.72 mmol of benzoylformyl chloride, which was freshly prepared in a separate reaction flask at ambient temperature from 2.66 g (17.72 mmol) of benzoylformic acid and 2.3 mL (26.37 mmol) of oxalyl chloride in 18.0 mL of methylene chloride containing a catalytic amount of dimethylformamide. The reaction mixture was stirred at 25° C. overnight at which time the mixture was poured into 1.0N HCl. The aqueous layer was discarded and the organic layer was washed twice with saturated sodium bicarbonate. The combined aqueous layers were washed with methylene chloride, acidified to pH 2.0 with concentrated HCl, and then extracted repeatedly with ether. Flash chromatography (Still, W. C. et al., *J. Org. Chem.* 43:2923 (1978)) (elution with 1:1 ethyl acetate-hexane containing 1% acetic acid provided 2.3 g of (S)-N-(phenylglyoxyl)-pipecolic acid (135) as a rotameric mixture. $^1$H NMR (500 MHz, CDCl$_3$) $\delta$11.4–11.1 (br s), 8.02 (d), 7.98 (d), 7.65 (t), 7.58–7.43 (m), 5.45 (d), 4.64 (dd), 4.43 (d), 3.52 (dd), 3.25 (ddd), 3.01 (ddd), 2.42 (d), 2.24 (d), 1.86–1.78 (m), 1.68–1.38 (m).

3. cis-and trans-4-(tert-Butyldimethylsilyloxy)cyclohexane-1-ol (136) and (137)

To a solution of 3.43 g (21.7 mmol) of cis- and trans-methyl 4-hydroxycyclohexane carboxylate (Noyce, D. S. and D. B. Denney, *J. Am. Chem. Soc.* 74:5912 (1952)) in 45 mL of methylene chloride at 0° C. was added 3.0 mL (26.0 mmol) of 2,6-lutidine followed by 5.5 mL. (23.8) mmol of tert-butyldimethylsilyl trifluoromethanesulfonate. The ice bath was removed and the reaction mixture was allowed to stir at 25° C. for 2 h at which time the solution was poured into saturated sodium bicarbonate. The layers were partitioned and the organic layer was washed with saturated copper sulfate and water and then dried over MgSO$_4$ to give 5.9 g of the crude methyl esters. A solution of 5.72 g (21.0 mmol) of this mixture in 45 mL of anhydrous THF was treated with 400 mg (10.5 mmol) of lithium aluminum hydride. The reaction mixture was stirred at 25° C. for 0.5 h and was then quenched by the slow addition of a saturated solution of Rochelle's salt. The mixture was diluted with ether, the layers were partitioned and the aqueous layer was washed twice with ethyl acetate. The combined organic extracts were dried over MgSO$_4$ and concentrated to give 4.9 g of the diastereomeric alcohols. Flash chromatography (elution with 1:5 ethyl acetate-hexane) gave 650 mg of (136), 1.10 g of (137) and 2.40 g of a mixture of the two. Data for (136): $^1$H NMR (300 MHz, CDCl$_3$) $\delta$3.99–3.92 (m), 3.46 (d), 1.72–1.58 (m), 1.57–1.36 (m), 0.86 (s), 0.08 (s). Data for (137): $^1$H NMR (300 MHz, CDCl$_3$) $\delta$3.47

(dddd), 3.38 (d), 1.86–1.67 (m), 1.47–1.16 (m), 1.05–0.77 (m), 0.72 (s), −0.02 (s).

4. (E)-Ethyl 3-[cis-(4-tert-Butyldimethylsilyloxycyclohexyl)]- 2-methylprop-2-enoate (138)

To a −78° C. solution of oxalyl chloride (465 µL, 5.33 mmol) in 5.0 mL of methylene chloride was added dimethylsulfoxide (755 µL, 10.65 mmol). The resulting solution was stirred for 5 min and then 650 mg (2.66 mmol) of the alcohol (136) was added in 5.0 mL of methylene chloride. The reaction mixture was stirred at −78° C. for 45 min at which time 2.2 mL (16.0 mmol) of triethylamine was added and the solution was allowed to warm to ambient temperature. The reaction was quenched with 1.0N HCl and the aqueous layer was extracted with three portions of methylene chloride. The. combined organic extracts were dried over MgSO$_4$ and evaporated to dryness to give 620 mg of the intermediate aldehyde which was treated directly with 1.22 g (3.36 mmol) of (carbethoxyethylidine)triphenylphosphorane in 5.0 mL of methylene chloride. The resulting reaction mixture was stirred at ambient temperature overnight and wathen poured into water. The layers were partitioned and the aqueous layer was extracted twice with methylene chloride. The combined organic layers were dried over MgSO$_4$ and concentrated to yield 1.55 g of crude product. Flash chromatography (elution with 1:20 ether-hexane) gave 300 mg of the enoate (138) as an oil.

5. (E)-3-[cis-(4-tert-Butyldimethylsilyloxycyclohexyl)]- 2-methylprop-2-en-1-ol (139)

To a solution of 300 mg (0.95 mmol) of enoate (138) in 2.0 mL of anhydrous tetrahydrofuran at 25° C. was added 18 mg (0.43 mmol) of lithium aluminum hydride and the resulting solution was allowed to stir for 30 min. The reaction was quenched by the slow addition of saturated Rochelle's salt and diluted with ethyl acetate. The layers were separated and the aqueous layer was extracted with two portions of ethyl acetate. The combined organic extracts were washed with water and brine and then dried over MgSO$_4$. Evaporation and flash chromatography (elution with 1:10 ethyl acetate-hexane) gave 220 mg of the allyic alcohol (139). $^1$H NMR (300 MHz, CDCl$_3$) δ5.34 (d), 3.96 (d), 3.85 (m), 2.26–2.18 (m), 1.64 (d), 1.61–1.34 (m), 1.82 (s), 0.0 (s).

6. (E)-3-[cis-(4-tert-Butyldimethylsilyloxycyclohexyl)]- 2-methylprop-2-enyl N-(phenylglyoxyl)pipecolate (140)

To a solution of 68 mg (0.24 mmol) of allylic alcohol (139), 42.3 mg (0.16 mmol) of acid (135) and 39.8 mg (0.20 mmol) of 1-(3-dimethylamino-propyl)-3-ethylcarbodiimide hydrochloride (EDC) in 2.0 mL of anhydrous methylene chloride was added a catalytic amount of 4-dimethylaminopyridine and the resulting mixture was stirred overnight at room temperature. The reaction mixture was then poured into water, the layers partitioned and the aqueous layer was extracted twice with methylene chloride. The combined organic extracts were dried over MgSO$_4$ and concentrated to yield a yellow oil. Flash chromatography (elution with 15% ethyl acetate in hexane) gave 9.2 mg of the ester (140) as a rotameric mixture. $^1$H NMR (500 MHz, CDCl$_3$) δ8.01 (d), 7.94 (d), 7.59–7.52 (m), 7.46–7.39 (m), 7.19 (d), 7.12 (d), 6.82 (d), 6.51 (s), 6.38 (s), 5.43 (d), 4.78 (ABq), 4.62 (dd), 4.58 (s), 4.41 (d), 3.51 (dd), 3.23 (ddd), 3.01 (ddd), 2.41 (d), 2.24 (d), 1.91 (s), 1.84–1.76 (m), 1.65–1.48 (m), 0.96 (s), 0.18 (s).

7. (E)-3-[cis-4-(hydroxycyclohexyl)]-2-methylprop-2-enyl N-(phenylglyoxyl)-ipecolate (25)

To a solution of 9.2 mg (0.02 mmol) of ester (140) in 1.0 mL of acetonitrile at 25° C. was added dropwise a solution consisting of a 95:5 mixture of acetonitrile: 48% hydrofluoric acid and the reaction was stirred until thin layer chromatography (TLC) indicated the disappearance of starting material. The reaction was quenched by the addition of saturated potassium carbonate. The reaction mixture was extracted with three portions of ethyl acetate, dried over MgSO$_4$ and concentrated. Flash chromatography (elution with 35% ethyl acetate in hexane) yielded 6.1 mg (82%) of the ester (25) as a rotameric mixture. $^1$H NMR (500 MHz, CDCl$_3$) δ8.02 (dd), 7.97 (dd), 7.67–7.59 (m), 7.56–7.48 (m), 5.49 (d), 5.44 (d), 4.61 (ABq), 4.44 (s), 4.41 (d), 3.98–3.91 (m), 3.5 (br d), 3.26 (ddd), 3.11 (ddd), 2.43–2.18 (m), 1.86–1.37 (m), 1.72 (d), R$_f$ 0.57 (3:1 ethyl acetate-hexane)

EXAMPLE 2

Synthesis of (S)-Benzyl N-(phenylglyoxyl)pipecolate (3)

To a solution of 43 mg (0.19 mmol) of freshly generated (S)-Benzyl pipecolate (133) (described in Example 1) in 2.0 mL of anhydrous methylene chloride was added 44 mg (0.29 mmol) of benzoylformic acid and 56 mg (0.29 mmol) of 1-(3-dimethylamino-propyl)-3-ethylcarbodiimide hydrochloride (EDC) and the resulting mixture was stirred overnight at room temperature. The reaction mixture was then poured into water, the layers partitioned and the aqueous layer was extracted twice with methylene chloride. The combined organic extracts were dried over MgSO$_4$ and concentrated to yield a yellow oil. Flash chromatography (elution with 1:3 ether-hexane) gave 49 mg (72%) of the keto-amide (3) as a rotameric mixture. $^1$H NMR (500 MHz, CDCl$_3$) δ7.98 (d), 7.91 (d), 7.58 (t), 7.41–7.30 (m), 5.45 (d), 5.21 (ABq), 5.06 (ABg), 4.61 (dd), 4.42 (d), 3.48 (dd), 3.19 (ddd), 2.96 (ddd), 2.40 (d), 2.21 (d), 1.83–1.72 (m), 1.61–1.49 (m), 1.46–1.33 (m), R$_f$ 0.55 (1:1 ether-hexane).

EXAMPLE 3

Synthesis of (S)-Benzyl N-[(3-methoxyphenyl)glyoxyl)]pipecolate (9)

The keto-amide (9) was prepared from 45 mg (0.205 mmol) of (S)-Benzyl pipecolate (133) (described in Example 1) and 55 mg (0.306 mmol) of 3-methoxybenzoylformic acid (Barnish, T. et al., *J. Med. Chem.* 24:339 (1981)) as described in Example 2. Flash chromatography (elution with 1:4 ether-hexane) gave 73 mg (93%) of (9) as a rotameric mixture. $^1$H NMR (300 MHz, CDCl$_3$) δ 7.59–7.10 (m), 5.42 (d), 5.23 (ABq), 5.09 (ABq), 4.59 (dd), 4.38 (d), 3.82 (s), 3.81 (s), 3.48–3.40 (m), 3.20 (ddd), 2.98 (ddd), 2.39 (d), 2.21 (d), 1.82–1.70 (m), 1.61–1.22 (m), R$_f$ 0.45 (1:1 ether-hexane).

EXAMPLE 4

Synthesis of (S)-Benzyl N-(2-furylglyoxyl)pipecolate (20)

To a 0° C. solution of 412 mg (1.03 mmol) of (S)-Benzyl pipecolate salt (134) (described in Example 1) in 40 mL of acetonitrile was added 198 µL (1.14 mmol) of diisopropylethylamine, 174 mg (1.24 mmol) of α-oxo-2-furanacetic acid, 579 mg (1.24 mmol) of benzotriazol-1-yloxytris(dimethylamino)phosphonium hexafluorophosphate and then 216 µL (1.24 mol) of diisopropylethylamine. The resulting reaction mixture was stirred at ambient temperature for 14 h and then evaporated to dryness. The residue was dissolved into 50 mL of ethyl acetate, washed sequentially with 50 mL of 0.5N HCl, 50 mL of saturated NaHCO$_3$, 50 mL of brine and was then dried over MgSO$_4$ and concentrated- Flash chromatography (elution with 2% ether in methylene chloride) provided 163 mg (46%) of the keto-amide (20) as an oil. The $^1$H NMR spectrum of this coinpound (300 MHz, CDCl$_3$) was consistent with the product as a mixture of rotamers. R$_f$ 0.2 (2% ether in methylene chloride). HPLC R$_t$=12.83 min.

EXAMPLE 5

Synthesis of (S)-Benzyl N-(4-Methoxycinnamoyl)pipecolate (112)

To a solution of 145 mg (0.37 mmol) of (S)-Benzyl pipecolate salt (134) (described in Example 1) in 8.0 mL of methylene chloride was added 102 mg (0.57 mmol) of 4-methoxycinnamic acid, 107 mg (0.55 mmol) of 1-(3-dimethylaminopropyl)- 3-ethylcarbodiimide hydrochloride (EDC) and 130 μL (0.74 mmol) of diisopropylethylainine, The resulting solution was stirred at ambient temperature for 12 h and was then concentrated under reduced pressure. Flash chromatography (elution with 1:1 ethyl acetate-hexane) gave 91 mg (65%) of the amide (112) as a colorless oil. $^1$H NMR (300 MHz, CDCl$_3$) δ7.66 (d), 7.50 (d), 7.35 (m), 6.90 (d), 6.82 (d), 6.63 (d), 5.55 (d), 5.20 (br s), 4.86 (br s), 4.67 (br d) 4.03 (br d), 3.83 (s), 3.37 (dt), 2.78 (dt) 2.33 (br d), 1.74 (m), 1.43 (m). R$_f$ 0.40 (1:1 ether-hexane).

EXAMPLE 6

Synthesis of (S)-3-(3,4-Methylenedioxyphenyl)-prop-2-enoylproline benzyl ester (109) and (S)-3-(3,4-Methylenedioxyphenyl)-prop-2-enoylalanine benzyl ester (132)

A solution of 192 mg (1.0 mmol) of 3,4-methylenedioxycinnamic acid, 121 mg (0.5 mmol) of proline benzyl ester hydrochloride and 108 mg (0.5 mmol) of alanine benzyl ester hydrochloride in 6 mL of acetonitrile was treated sequentially with 0.35 mL (2.0 mmol) of diisopropylethylamine and 443 mg (1.0 mmol) of benzotriazol-1-yloxytris-(dimethylamino)phosphonium hexafluorophosphate. The mixture was stirred for 16 hrs then concentrated in vacuo. The residue was dissolved in 10 mL of dichloromethane and poured into 3 volumes of diethyl ether. The mixture was washed sequentially with water, 10% potassium bisulfate solution, water, saturated sodium bicarbonate solution, water and saturated sodium chloride solution. The organic layer was dried over magnesium sulfate, filtered and concentrated in vacuo. The residue was purified by silica gel column chromatography, using a stepwise gradient of 30%, 35%, 40%, and 45% ethyl acetate in hexane as eluant. Ester (109) (142 mg) was obtained as a colorless oil, Rf=0.4 (40% ethyl acetate/hexane); HPLC, R$_t$=12.26; $^1$H NMR (300 MHz) consistent with structure. Ester (132) (162 mg) was obtained as a colorless oil; TLC, R$_f$=0.22 (40% ethyl acetate/hexane); HPLC; R$_t$=11.84 min; $^1$H NMR (300 MHz) consistent with structure.

EXAMPLE 7

Synthesis of (S)-N-3-(4-methoxyphenyl)-prop-2-enoyl-N-methylalanine benzyl ester (129).

1. (S)-N-Methylalanine benzyl ester p-toluene sulfonic acid salt (141)

A suspension of 1.55 g (15.0 mmol) of (S)-N-methylalanine and 9.31 (90.0 mmol) of benzyl alcohol in 30 mL of toluene was treated with 3.00 g (15.8 mmol) of p-toluenesulfonic acid monohydrate. The mixture was heated for 19 hours under reflux with removal of water via a Dean-Stark trap. After cooling, the reaction solution was poured into 200 mL of ether, precipitating a yellow oil. The solvents were decanted and the residue was taken up into ethyl acetate and concentrated to yield a viscous, light yellow oil (141); TLC: R$_f$=0.34, 95:5:0.5 CH$_2$Cl$_2$/MeOH/concentrated ammonium hydroxide; $^1$H NMR (300 MHz) consistent with structure.

2. (S)-N-3-(4-methoxyphenyl)-prop-2-enoyl-N-methylalanine benzyl ester (129)

A suspension of 96 mg (0.5 mmol) of 4-methoxycinnamic acid and 121 mg (0.5 mmol) of (141) in 6 mL of dichloromethane was cooled in an ice/water bath under nitrogen. The mixture was treated with 0.26 mL (1.5 mmol) of diisopropylethylamine and 135 mg (0.53 mmol) of N,N-bis-(2-oxo-3-oxazolidinyl) phosphinic chloride and then stirred for 16 hours, warming slowly to ambient temperature. The mixture was poured into three volumes of diethyl ether and washed sequentially with water, 10% potassium bisulfate solution, water, saturated sodium bicarbonate solution, water, and saturated sodium chloride solution. The organic layer was dried over magnesium sulfate, filtered, and concentrated in vacuo. The residue was purified by preparatie thick layer silica gel chromatography using 40% ethyl acetate/hexane as eluant. Ester (129) (40 mg) was obtained as a yellow oil: TLC, R$_f$=0.24 (35% ethyl acetate/hexane); HPLC, R$_t$=13.34 min; $^1$H NMR (300 MHz) consistent with structure.

EXAMPLE 8

Synthesis of (S)-N-Methyloxalyl-N-ethylalanine benzyl ester (127)

1. (S)-N-9-Fluorenylmethoxycarbonyl-N-ethylalanine benzylester (142)

A suspension of 848 mg (2.5 mmol) of (S)-N-Fmoc-N-ethylalanine in 10 mL Of dichloromethane was treated with 436 μL (5.0 mmol) of oxalyl chloride followed by a catalytic amount (1 drop) of dimethylformamide. The mixture was stirred for one hour, then concentrated in vacuo. The yellow, oily residue was treated with 10 mL of toluene followed by 517 mg (0.5 mmol) of benzyl alcohol and 669 mg (5.0 mmol) of silver cyanide. The mixture was heated in an 80° C. oil bath with vigorous stirring for 20 minutes, then cooled and filtered through a pad of diatomaceous earth. The liltrate was concentrated, and the residue was purified by silica gel column chromatography, using 10% acetone in hexane as eluant. Ester (142) (810 mg) was obtained as a colorless oil; TLC: R$_f$=0.28, 15% acetone/hexane; $^1$H NMR (300 MHz) consistent with structure.

2. (S)-N-Methyloxalyl-N-ehylalanine benzyl ester (127)

A solution of 0.25 g (0.58 mmol) of (142) in 3 mL of acetonitrile was treated with 3 mL of diethylamine and the mixture was allowed to stand for 20 min. The mixture was concentrated in vacuo and the residue was taken up in 10 mL of acetonitrile and again evaporated. After repeating this process, the residue was dissolved in 4 mL of dichloromethane, cooled in an ice/water bath under nitrogen, and treated with 111 μL (0.64 mmol) of diisopropylethylamine followed, during approximately 1 min. with 54 μL (0.64 mmol) of methyl oxalyl chloride. The mixture was stirred overnight, warming slowly to ambient temperature, then poured into three volumes of ether. The mixture was washed sequentially with water, 10% potassium bisulfate solution, water, saturated sodium bicarbonate solution, water, and saturated sodium chloride solution. The organic layer was dried over magnesium sulfate, filtered, and concentrated in vacuo. The residue was purified by silica gel column chromatography using 1:7 acetone: hexane as eluant. Ester (127) (147 mg) was obtained as a colorless oil, $R_f$=0.36, 35% acetone/hexane; HPLC, $R_t$=12.19 min; $^1$H NMR (300 MHz) consistent with structure.

EXAMPLE 9

Synthesis of (S)-3-Cyclopentylpropyl N-(2-Methyloxalyl)pipecolate (135)

1. (S)-N-(Methyloxalyl)pipecolic Acid (143)

The acid (143) was prepared from methyl oxalyl chloride as described in Example 1 for the production of (S)-N-(Phenylglyoxyl)pipecolic acid (135). Thus, 3.16 g (11.32 mmol) of the tartrate salt of (S)-pipecolic acid and 1.19 mL (12.45 mmol) of methyl oxalyl chloride gave 1.25 g (51%) of the acid (143) as a an solid. $^1$H NMR (300 MHz, CDCl$_3$) δ5.31 (d), 4.62 (d), 4.49 (br d), 3.61 (br d), 3.90 (s), 3.88 (s), 3.46 (dt), 2.97 (dt), 2.40–1.40 (m).

2. (S)-3-Cyclopentylpropyl N-(2-Methyloxalyl)pipecolate (35)

The ester (35) was prepared from 3-cyclopentylpropan-1-ol and the acid (143) as described in Example 2. Flash chromatography (elution with 2% ether in methylene chloride) gave 72 mg (48%) of (35) as a colorless oil. The $^1$H NMR spectrum of this compound (300 MHz, CDCl$_3$) was consistent with the product as rotamers. $R_f$ 0.56 (10% ether in methylene chloride). HPLC, $R_t$=14.30 min.

DISCUSSION OF ASSAYS

Cell Source and Culture

Fresh peripheral blood lymphocytes (PBLs) from Leuko-Pak cells or whole blood from random normal blood donors (tested HIV-negative and hepatitis negative) are isolated and separated by density centrifugation over Histopaque 1077 (Sigma Chemical Co., St. Louis, Mo.). The murine CTLL cytotoxic T cell line and the human Jurkat T cell line are from ATCC (CTLL-2 ATCC TIB214, JURKAT CLONE E6-1 ATCC TIB152). The human allogeneic B cell lines used for activation of the fresh PBLs are EBV-transformed lymphocytes from normal healthy adult donors with two completely different HLAhaplotypes. All cell lines were routinely tested for the presence of Mycolasma contamination using the GibcoMycotect test kit and are Mycolasma-free. Culture medium consksts of RPMI 1640 (Gibco, Grand Island, N.Y.) containing penicillin (50 U/ml) and streptomycin (50 µg/ml), L-glutamine 2 mM, 2 mercaptoethanol (5×10$^{-5}$), 10% heat-inactivated FCS and 10 mM HEPES.

Compound Solutions and Titrations

All chemical stocks were dissolved in DMSO. Titrations of compounds were made into the medium the individual assay was carried out in, i.e., complete RPMI or HB 104 for final diluted concentrations, using multiple three-fold dilutions from 1 µM or 10 µM stock solutions.

MTT Assay

The MTT assay is a colorimetric technique to determine the toxicity of the compounds on growing lymphold and non-lymphoid cell lines based on reduction of the tetrazolium salt by intact mitochondria (Mossman, T., *J. Immunol. Methods* 65:55 (1983)). Cell viability in the presence or absence of different concentrations of test compounds in serum-free medium (HB 104, HANA Biologic, Inc.) was assessed using MTT (3-[4,5-dimethyl -thiazoyl-2-yl]2,5-diphenyl-tetrazolium bromide). At 4 h before the end of the 3-day toxicity assay culture period, 20 µl of MTT dye (5 mg/ml in pH 7.2 PBS) were added to each microtiter well. At the end of the incubation time, most of the culture media was carefully aspirated out of each well. Then 100 µl of acidified isopropyl alcohol (0.04N HCl) was adde to solubilize the dye and optical density is read at 570 nm minus OD at 630 nm (Molecular Devices Thermomax plate reader and Softmax software program, Menlo Park, Calif.). Results were compared with mean OD in controls (medium with no drugs) and doses causing 50% toxicity ($TC_{50}$) were calculated.

Mitogenesis Assays ("PMA" and "OKT3")

The inhibitory effect of test compounds on the proliferation of human PBLs in response to mitogens (Waithe, W. K. and K. Hirschhorn, *Handbook of Experimental Immunology*, 3d Ed. Blackwell Scientific Publications, Oxford (1978); Mishell, B. B. and S. M. Shiigi, *Selected Methods in Cellular Immunology* W. H. Freeman and Co., San Francisco, Calif. (1980)) was assessed by stimulation of 5×10$^4$ cells with OKT3 (10$^{-4}$ dilution final) or PMA (10 ng/ml) plus ionomycin (250 ng/ml) in the presence or absence of different concentrations of test compounds and control drugs (CsA, FK506, Pagamycin) in final volume of 200 µl per well in 96 well round bottomed plates. After 48 h incubation (37° C., 5% CO$_2$), cells were pulsed with 1 µCi of $^3$H-thymidine, harvested 24 h later with a Tom Tek cell harvester, and counted in LKB β-scintillation counter. Results (cpm) were compared with controls with medium alone, and concentrations causing 50% reduction in counts ($IC_{50}$) were calculated.

MLR Bioassays ("LB" and "JVM")

Antigen activated proliferation of PBLs in a primary mixed lymphocyte reaction was assessed in the presence or absence of different concentrations of tested compounds and control drugs. 5×10$^4$ fresh PBLs were stimulated with 5×10$^3$ of Mitomycin C treated-allogeneic EBV-transformed β-lymphoglastoid cells, IB and JVM, in a final volume of 200 µl per well in 96-well round-bottomed plates (Mishell, B. B. and S. M. Shiigi, *Selected Methods in Cellular Immunology* W. H. Freeman and Co., San Francisco, Calif. (1980); Nelson, P. A. et al., *Transplantation* 50:286 (1990)). Cultures were pulsed on day 6, harvested 24 h later and counted as in previous section.

IL-2 Microassay ("CTLL")

To determine if test compounds inhibit the later T cell activation process of cytokine utilization, the proliferative response of the IL-2 dependent CTLL-20 murine T cell line (ATCC) was assessed (Gillis, S. et al., *J. Immunology* 120:2027 (1978)). CsA and FK506 inhibit the production of IL-2 by activated-T cells, whereas Rapamycin interferes with the utilization of IL-2. Rapamycin thus inhibits IL-2 dependent proliferation of the CTLLs, and CsA and FK506 do not (Dumont, F. J. et al., *J. Immunology* 144:251 (1990)). 3×10$^3$ CTLLs were exposed to different concentrations of test compounds and control drugs in the presence of 1 U/ml of human recombinant IL-2 (Genzyme, rIL-2) for 24 h. Four h after adding drugs, cells were pulsed with 1 µCI of 3H-thymidine, incubated for an additional 20 h (37° C., 5% CO$_2$), and then harvested and counted as previously described.

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A method of suppressing graft rejection in an individual, comprising the step of administering to the individual a composition comprising an immunosuppressant compound that binds to FK-506 binding protein and having a molecular weight below 750 atomic mass units in an amount effective to reduce or eliminate an immune response, in a physiologically acceptable vehicle, wherein the immunosuppressant compound is represented by the formula:

and pharmaceutically acceptable salts thereof, wherein A in O, NH, or N-(C1–C4 alkyl);

wherein B is hydrogen, CHL—Ar, (C1–C6)-straight or branched alkyl, (C2–C6)-straight or branched alkenyl, (C5–C7)-cycloalkyl, (C5–C7)-cycloalkenyl or Ar substituted (C1–C6)-alkyl or (C2–C6)-alkenyl, or wherein L and Q are independently hydrogen, (C1–C6)-straight or branched alkyl or (C2–C6)-straight or branched alkenyl;

wherein T is Ar or substituted cyclohexyl with substituents at positions 3 and 4 which are independently selected from the group consisting of hydrogen, hydroxyl, O-(C1–C4)-alkyl or O-(C2–C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1–C6)-straight or branched alkyl or (C2–C6)-straight or branched alkenyl, O-(C1–C4)-straight or branched alkyl or O-(C2–C4)-straight or branched alkenyl, O-benzyl, O-phenyl, amino and phenyl;

wherein D is U; E is either oxygen or CH-U, provided that if D is hydrogen, then E is CH-U or if E is oxygen then D is not hydrogen;

wherein U is hydrogen, O-(C1–C4)-straight or branched alkyl or O-(C2–C4)-straight or branched alkenyl, (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, 2-indolyl, 3-indolyl, (C1–C4)-alkyl-Ar, (C2–C4)-alkenyl-Ar or Ar;

wherein J is hydrogen or C1 or C2 alkyl; K is (C1–C4)-straight or branched alkyl, benzyl or cyclohexylmethyl; and wherein the stereochemistry at carbon position 1 is S.

2. The method according to claim 1, wherein the graft rejection results from a bone marrow or organ transplant.

3. The method of claim 1, wherein the immunosuppressant compound has a molecular weight below about 500 amu.

4. A method of preventing or significantly reducing autoimmune response in a mammal, comprising the step of administering to the mammal a composition comprising an immunosuppressant compound that binds to FK-506 binding protein and having a molecular weight below 750 atomic mass units in an amount effective to reduce or eliminate an immune response, in a physiologically acceptable vehicle, wherein the immunosuppressant compound is represented by the formula:

and pharmaceutically acceptable salts thereof, wherein A in O, NH, or N-(C1–C4 alkyl);

wherein B is hydrogen, CHL—Ar, (C1–C6)-straight or branched alkyl, (C2–C6)-straight or branched alkenyl, (C5–C7)-cycloalkyl, (C5–C7)-cycloalkenyl or Ar substituted (C1–C6)-alkyl or (C2–C6)-alkenyl, or wherein L and Q are independently hydrogen, (C1–C6)-straight or branched alkyl or (C2–C6)-straight or branched alkenyl;

wherein T is Ar or substituted cyclohexyl with substituents at positions 3 and 4 which are independently selected from the group consisting of hydrogen, hydroxyl, O-(C1–C4)-alkyl or O-(C2–C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1–C6)-straight or branched alkyl or (C2–C6)-straight or branched alkenyl, O-(C1–C4)-straight or branched alkyl or O-(C2–C4)-straight or branched alkenyl, O-benzyl, O-phenyl, amino and phenyl;

wherein D is U; E is either oxygen or CH-U, provided that if D is hydrogen, then E is CH-U or if E is oxygen then D is not hydrogen;

wherein U is hydrogen, O-(C1–C4)-straight or branched alkyl or O-(C2–C4)-straight or branched alkenyl, (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, 2-indolyl, 3-indolyl, (C1–C4)-alkyl-Ar or (C2–C4)-alkenyl-Ar or Ar;

wherein J is hydrogen or C1 or C2 alkyl; K is (C1–C4)-straight or branched alkyl, benzyl or cyclohexylmethyl; and wherein the stereochemistry at carbon position 1 is S.

5. A method of claim 4, wherein the mamal is a human.

6. The method according to claim 1, wherein said immunosuppressant compound is selected from:

wherein B, D, J and K are defined below:

| No | B | D | J | K | Ki | $K_d$ |
|---|---|---|---|---|---|---|
| 124 | Benzyl | Methoxy | Methyl | Hydrogen | 1000 μM | >200 μM |
| 125 | Benzyl | Methoxy | Methyl | S-Methyl | 400 μM | >200 μM |
| 126 | Benzyl | Methoxy | Methyl | S-Isopropyl | 170 μM | >200 μM |
| 127 | Ethyl | Methoxy | Benzyl | Hydrogen | >1200 μM | >300 μM |
| 128 | tert-Butyl | Methoxy | Ethyl | S-Methyl | >400 μM | >500 μM | or wherein B, U, J and K are defined below:

| No | B | U | J | K | Ki | $K_d$ |
|---|---|---|---|---|---|---|
| 129 | Benzyl | 4-Methoxyphenyl | Methyl | S-Methyl | 80 μM | >150 μM |
| 130 | Benzyl | 4-Methoxyphenyl | Methyl | S-Isopropyl | 30 μM | >20 μM |
| 131 | Benzyl | 3,4-Methylenedioxyphenyl | Methyl | S-Methyl | 50 μM | ND |
| 132 | Benzyl | 3,4-Methylenedioxyphenyl | Hydrogen | S-Methyl | 60 μM | ND |

7. The method according to claim 4, wherein said immunosuppressant compound is selected from:

wherein B, D, J and K are defined below:

| No | B | D | J | K | Ki | $K_d$ |
|---|---|---|---|---|---|---|
| 124 | Benzyl | Methoxy | Methyl | Hydrogen | 1000 μM | >200 μM |
| 125 | Benzyl | Methoxy | Methyl | S-Methyl | 400 μM | >200 μM |
| 126 | Benzyl | Methoxy | Methyl | S-Isopropyl | 170 μM | >200 μM |
| 127 | Ethyl | Methoxy | Benzyl | Hydrogen | >1200 μM | >300 μM |
| 128 | tert-Butyl | Methoxy | Ethyl | S-Methyl | >400 μM | >500 μM | or wherein B, U, J and K are defined below:

| No | B | U | J | K | Ki | $K_d$ |
|---|---|---|---|---|---|---|
| 129 | Benzyl | 4-Methoxyphenyl | Methyl | S-Methyl | 80 μM | >150 μM |
| 130 | Benzyl | 4-Methoxyphenyl | Methyl | S-Isopropyl | 30 μM | >20 μM |
| 131 | Benzyl | 3,4-Methylenedioxyphenyl | Methyl | S-Methyl | 50 μM | ND |
| 132 | Benzyl | 3,4-Methylenedioxyphenyl | Hydrogen | S-Methyl | 60 μM | ND |

8. The method according to claim 4, wherein the immunosuppressant compound has a molecular weight below 500 amu.

* * * * *

UNITED STATES PATENT AND TRADEMARK OFFICE
CERTIFICATE OF CORRECTION

PATENT NO. : 5,516,797
DATED : May 14, 1996
INVENTOR(S) : David M. Armistead, et al Page 1 of 3

It is certified that error appears in the above-identified patent and that said Letters Patent is hereby corrected as shown below:

Column 1, line 10 delete "U.S. Pat. No. 5,192773" and substitute therefor -- U.S. Pat. No. 5,192,773 --.
Column 1, line 65 delete "56:" and substitute therefor --256:--.
Column 2, line 7 delete "Aplasti" and substitute therefor
-- Aplastic --.
Column 2, line 9 and column 15, line 43 delete "coliris" and substitute therefor -- colitis --.
Column 2, line 30 delete "scierosis." and substitute therefor
-- sclerosis. --.
Column 2, line 41 delete "382-382" and substitute therefor
-- 382-383 --.
Column 2, line 65 delete "autoimmures" and substitute therefor
-- autoimmune --.
Column 3, line 29 delete "sire" and substitute therefor --sive--.
Column 3, line 32 and column 15, line 19 delete "(rotamass)" and substitute therefor -- (rotamase) --.
Column 4, line 57 delete "rosylate," and substitute therefor
-- tosylate, --.
Column 4, line 66 delete "dibtyl" and substitute therefor
--dibutyl--.
Column 11, line 25 delete "imunosuppreseive" and substitute therefor -- immunosuppressive --.
Column 11, line 55 delete "N-succinylAla-Ala-Pro-Phe-p-nitroanilide" and substitute therefor -- N-succinyl-Ala-Ala-Pro-Phe-p-nitroanilide --.
Column 12, line 27 delete "A 10" and substitute therefor -- A --.
Column 12, line 64 delete the duplicative line entirely.
Column 14, line 33 delete "immunosuppresive" and substitute therefor -- immunosuppressive --.
Column 14, line 43 delete "bythe" and substitute therefor
-- by the --.

UNITED STATES PATENT AND TRADEMARK OFFICE
CERTIFICATE OF CORRECTION

PATENT NO. : 5,516,797
DATED : May 14, 1996
INVENTOR(S) : David M. Armistead, et al It is certified that error appears in the above-identified patent and that said Letters Patent is hereby corrected as shown below:

Column 15, line 23 delete "immunosuppresstve" and substitute therefor -- immunosuppressive --.
Column 15, line 59 delete "adjuvnts" and substitute therefor -- adjuvants --.
Column 17, line 8 delete "asteroid," and substitute therefor -- a steroid, --.
Column 19, line 21 delete "wathen" and substitute therefor -- was then --.
Column 19, line 64 delete "ipecolate" and substitute therefor -- pipecolate --.
Column 21, line 5 delete "coinpound" and substitute therefor -- compound --.
Column 21, line 19 delete "diisopropylethylainine," and substitute therefor -- diisopropylethylamine. --.
Column 22, line 41 delete "Of" and substitute therefor -- of --.
Column 22, line 49 delete "liltrate" and substitute therefor -- filtrate --.
Column 22, line 55 delete "ehylalanine benzyl ester" and substitute therefor -- (S)-ethylalanine benzyl ester --.
Column 23, line 22 delete "a an" and substitute therefor --tan--.
Column 23, line 48 delete "HLAhaplotypes" and substitute therefor -- HLA haplotypes --.
Column 23, line 49 delete "Mycolasma" and substitute therefor -- Mycoplasma --.
Column 23, line 50 delete "Mycolasma-free." and substitute therefor -- Mycoplasma-free. --.

UNITED STATES PATENT AND TRADEMARK OFFICE
CERTIFICATE OF CORRECTION

PATENT NO. : 5,516,797
DATED : May 14, 1996
INVENTOR(S) : David M. Armistead, et al It is certified that error appears in the above-identified patent and that said Letters Patent is hereby corrected as shown below:

```
Column 23, line 51 delete "consksts" and substitute therefor
-- consists --.
Column 23, line 63 delete "lymphold" and substitute therefor
-- lymphoid --.
Column 27, line 5 delete "mamal" and substitute therefor
-- mammal --.
```

Signed and Sealed this

Ninth Day of January, 2001

Attest:

Q. TODD DICKINSON

Attesting Officer     Commissioner of Patents and Trademarks